US00PP16465P2

(12) United States Plant Patent
Fick

(10) Patent No.: US PP16,465 P2
(45) Date of Patent: Apr. 18, 2006

(54) ***SUTERA* PLANT NAMED 'MAXI MAUVE BLUE'**

(50) Latin Name: *Sutera halimifolia*
Varietal Denomination: Maxi Mauve Blue

(76) Inventor: Amanda Fick, P.O.Box 4183, George East, 6339 (ZA)

( * ) Notice: Subject to any disclaimer, the term of this patent is extended or adjusted under 35 U.S.C. 154(b) by 46 days.

(21) Appl. No.: 11/000,448

(22) Filed: Nov. 30, 2004

(51) Int. Cl.
*A01H 5/00* (2006.01)

(52) U.S. Cl. ..... Plt./263

(58) Field of Classification Search ..... Plt./263
See application file for complete search history.

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Sutera* plant named 'Maxi Mauve Blue', characterized by its outwardly spreading plant habit; vigorous growth habit; freely and continuous branching habit; freely flowering habit; large violet-colored flowers; and good garden performance.

1 Drawing Sheet

Botanical classification/cultivar designation: *Sutera halimifolia* cultivar Maxi Mauve Blue.

BACKGROUND OF THE INVENTION

The present Invention relates to a new and distinct cultivar of *Sutera* plant, botanically known as *Sutera halimifolia*, and hereinafter referred to by the cultivar name 'Maxi Mauve Blue'.

The new *Sutera* is a product of a planned breeding program conducted by the Inventor in George, South Africa. The objective of the breeding program is to create new *Suteras* with large and attractive flowers.

The new *Sutera* originated from a cross-pollination made by the Inventor in September, 1998 of two unnamed selections of *Sutera halimifolia*, not patented. The new *Sutera* was chosen as a single plant from the resulting progeny of the cross-pollination by the Inventor in July, 1999, in a controlled environment in George, South Africa.

Asexual reproduction of the new cultivar by terminal cuttings taken in George, South Africa since November, 2000, has shown that the unique features of this new *Sutera* are stable and reproduced true to type in successive generations.

SUMMARY OF THE INVENTION

Plants of the cultivar Maxi Mauve Blue have not been observed under all possible environmental conditions. The phenotype may vary somewhat with variations in environment such as temperature and light intensity without, however, any variance in genotype.

The following traits have been repeatedly observed and are determined to be the unique characteristics of 'Maxi Mauve Blue'. These characteristics in combination distinguish 'Maxi Mauve Blue' as a new and distinct cultivar of *Sutera:*

1. Outwardly spreading plant habit.
2. Vigorous growth habit.
3. Freely and continuous branching habit.
4. Freely flowering habit.

5. Large violet-colored flowers.
6. Good garden performance.

Compared to plants of the parent selections, plants of the new *Sutera* have larger and darker green-colored leaves and larger flowers. In addition, plants of the new *Sutera* and the parent selections differ in flower coloration.

Compared to plants of other selections of *Sutera halimifolia* known to the Inventor, plants of the new *Sutera* are more vigorous, more freely branching and have larger flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the colors of the new *Sutera.*

The photograph at the top of the sheet comprises a side perspective view of a typical flowering plant of 'Maxi Mauve Blue' grown in a 15-cm container.

The photograph at the bottom of the sheet comprises a close-up view of the typical flowers and leaves of 'Maxi Mauve Blue'.

DETAILED BOTANICAL DESCRIPTION

The aforementioned photographs and following observations and measurements describe plants grown in Bonsall, Calif., in an outdoor nursery under full sunlight conditions during the spring with day temperatures ranging from 18 to 35° C. and night temperatures ranging from 7 to 18° C. After planting rooted cuttings, plants were grown for about four weeks in 15-cm containers. Color references are made to The Royal Horticultural Society Colour Chart, 1995 Edition, except where general terms of ordinary dictionary significance are used.

Botanical classification: *Sutera halimifolia* cultivar Maxi Mauve Blue.

Parentage:

*Female parent*.—Unnamed selection of *Sutera halimifolia*, not patented.

*Male parent*.—Unnamed selection of *Sutera halimifolia*, not patented.

Propagation:

*Type cutting*.—Terminal vegetative cuttings.

*Time to initiate roots*.—About three weeks.

*Time to produce a rooted cutting*.—About four weeks.

*Root description*.—Fine; white in color.

*Rooting habit*.—Freely branching.

Plant description:

*Form*.—Outwardly spreading plant habit. Freely and continuously branching with about 15 lateral branches and numerous secondary lateral branches per plant. Vigorous growth habit.

*Plant height*.—About 18 cm.

*Plant diameter*.—About 50 cm.

*Lateral branches*.—Length: About 28 cm. Diameter: About 2 mm. Internode length: About 3 cm. Texture: Minute pubescence; rough. Color: 146A.

*Foliage description*.—Arrangement: Opposite; simple. Length: About 2.2 cm. Width: About 6 mm. Shape: Narrowly elliptic. Apex: Acute. Base: Clasping; sessile. Margin: Serrulate. Texture, upper and lower surfaces: Smooth, glabrous. Venation pattern: Pinnate. Color: Developing and fully expanded foliage, upper surface: 147A; venation, 147A. Developing and fully expanded foliage, lower surface: 147B; venation, 147B.

Flower description:

*Flower type and habit*.—Solitary axillary flowers; salverform; slender corolla tubes flare abruptly into five rounded lobes. Flowers persistent. Freely flowering; typically about 30 flower buds and open flowers per lateral branch. Flowers face mostly upward or outward. Flowers persistent.

*Natural flowering season*.—Plants typically flower from spring until fall; flowering continuous during this period.

*Flower longevity on the plant*.—About five days.

*Frangrance*.—None detected.

*Flower size*.—Diameter: About 1.5 cm. Depth: About 1 cm.

*Flower buds*.—Length: About 7 mm. Diameter: About 3.5 mm. Shape: Obovate. Color: 157A.

*Corolla*.—Quantity/arrangement: five fused petals; slender corolla tube flaring abruptly into five rounded lobes. Petal lobe length from throat: About 6 mm. Petal lobe width: About 4 mm. Petal lobe shape: Roughly spatulate. Petal lobe apex: Rounded. Petal lobe margin: Entire. Texture, upper and lower surfaces: Smooth, glabrous; velvety. Color: When opening, upper surface: 85C. When opening, lower surface: 85D. Fully opened, upper surface; 86B; color becoming closer to 85A with development. Fully opened, lower surface: 86D. Flower throat (inside): 24A. Flower tube (outside): 86D.

*Sepals*.—Arrangement/appearance: Single whorl of five sepals fused at base; star-shaped calyx. Length: About 5 mm. Width: Less than 1 mm. Shape: Narrow, linear. Apex: Acute. Margin: Entire. Texture, upper and lower surfaces: Pubescent, coarse; glandular. Color, upper and lower surfaces: 144A.

*Peduncles*.—Length: About 1 to 1.2 cm. Width: About 1 mm. Angle: About 45° from the stem. Strength: Moderately strong; slender. Texture: Smooth, glabrous. Color: 144A.

*Reproductive organs*.—Stamens: Quantity per flower: Four. Anther shape: Oval. Anther length: About 1 mm. Anther color: 160A. Pollen amount: Scarce. Pollen color: 14A. Pistils: Quantity per flower: One. Pistil length: About 1.2 cm. Style length: About 7 mm. Style color: 1D. Stigma shape: Elongated; curved. Stigma color: 2A. Ovary color: 144A.

*Seed/fruit*.—Seed and fruit production has not been observed.

Disease/pest resistance: Plants of the new *Sutera* have not been noted to be resistant to pathogens or pests common to *Sutera*.

Garden performance: Plants of the new *Sutera* have been observed to have good garden performance. Plants of the new *Sutera* tolerate temperatures from −4 to 38° C. and have good tolerance to wind and rain.

It is claimed:

1. A new and distinct cultivar of *Sutera* plant named 'Maxi Mauve Blue', as illustrated and described.

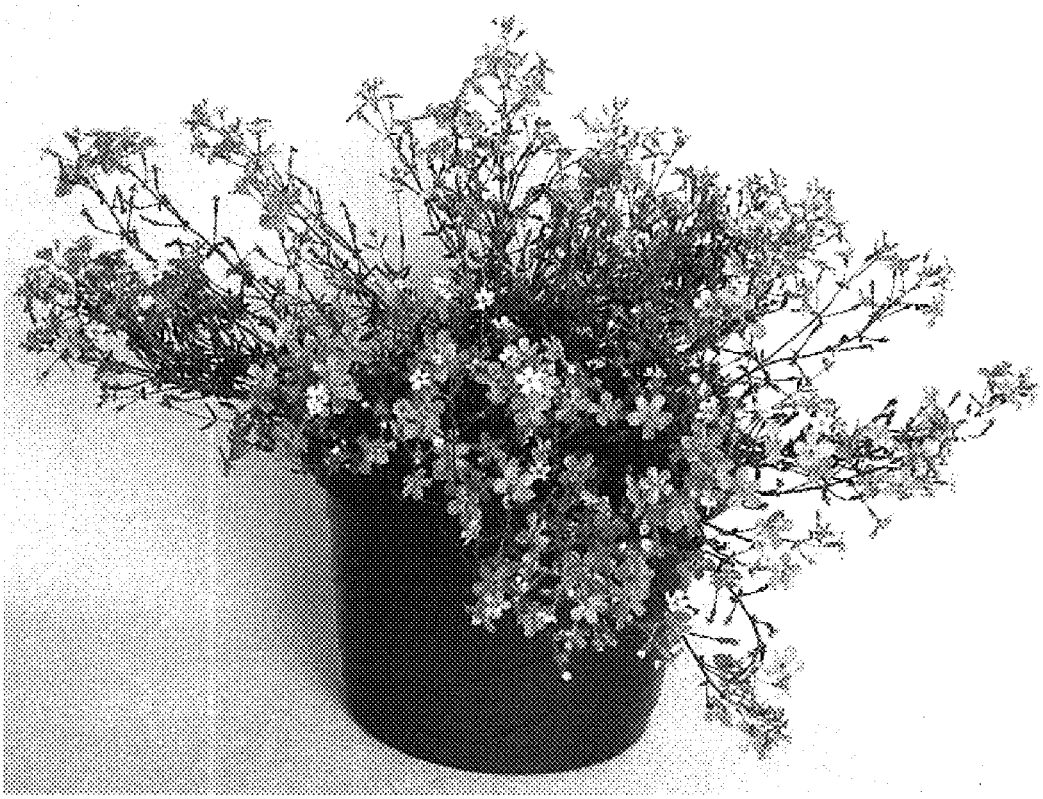
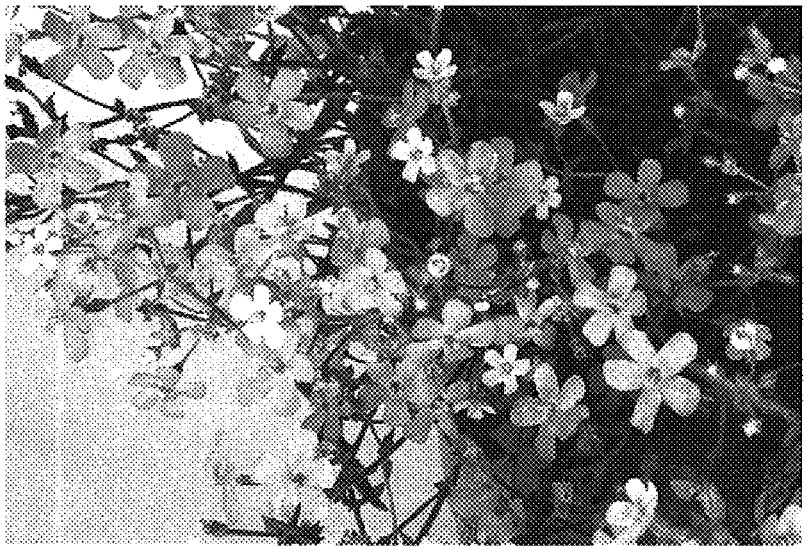

* * * * *